US009169551B2

(12) United States Patent  
Hauert et al.

(10) Patent No.: US 9,169,551 B2  
(45) Date of Patent: Oct. 27, 2015

(54) COATING FOR A COCRMO SUBSTRATE

(71) Applicant: Synthes USA, LLC, West Chester, PA (US)

(72) Inventors: Roland Hauert, Suhr (CH); Goetz Thorwarth, Duebendorf (CH); Claudiu Falub, Zurich (CH); Ulrich Mueller, Herrliberg (CH); Cyril Voisard, Langendorf (CH)

(73) Assignee: Depuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/655,518

(22) Filed: Oct. 19, 2012

(65) Prior Publication Data

US 2013/0060340 A1 Mar. 7, 2013

Related U.S. Application Data

(63) Continuation-in-part of application No. 13/087,013, filed on Apr. 14, 2011.

(60) Provisional application No. 61/324,664, filed on Apr. 15, 2010.

(51) Int. Cl.  
*C04B 41/88* (2006.01)  
*C23C 16/27* (2006.01)  
(Continued)

(52) U.S. Cl.  
CPC .............. *C23C 16/27* (2013.01); *A61L 27/045* (2013.01); *A61L 27/303* (2013.01); *A61L 27/306* (2013.01); *A61L 27/56* (2013.01); *C23C 14/165* (2013.01); *C23C 14/35* (2013.01); *C23C 16/0281* (2013.01); *C23C 16/26* (2013.01); *C23C 28/321* (2013.01); *C23C 28/322* (2013.01); *C23C 28/341* (2013.01); *C23C 28/343* (2013.01); *A61F 2310/0058* (2013.01); *A61L 2420/02* (2013.01); *A61L 2420/08* (2013.01);
(Continued)

(58) Field of Classification Search  
None  
See application file for complete search history.

(56) References Cited

U.S. PATENT DOCUMENTS 5,799,549 A 9/1998 Decker et al.  
6,740,393 B1 * 5/2004 Massler et al. ............... 428/216  
(Continued)

FOREIGN PATENT DOCUMENTS

CN 200680017994 5/2008  
JP 2007-510509 4/2007  
(Continued)

OTHER PUBLICATIONS

Alakoski, Esa, Mirjami Kiuru, Veli-Matti Tiainen, Asko Anttila, "Adhesion and quality test for tetrahedral amorphous carbon coating process," Diamond and Related Materials, vol. 12, Issue 12, Dec. 2003, pp. 2115-2118.*

(Continued)

*Primary Examiner* — Humera Sheikh  
*Assistant Examiner* — Daniel J Schleis  
(74) *Attorney, Agent, or Firm* — Morgan, Lewis & Bockius, LLP

(57) ABSTRACT

A coating for a CoCrMo substrate including a first layer located directly on the substrate and including $Ta(CoCrMo)_{0.5-2.0}$, a second layer located directly on the first layer and including tantalum, a third layer located directly on the second layer and including tantalum carbide, and a fourth layer located directly on the third layer and including diamond-like carbon (DLC).

20 Claims, 6 Drawing Sheets

(51) Int. Cl.

| | |
|---|---|
| *A61L 27/30* | (2006.01) |
| *A61L 27/04* | (2006.01) |
| *A61L 27/56* | (2006.01) |
| *C23C 14/16* | (2006.01) |
| *C23C 14/35* | (2006.01) |
| *C23C 16/02* | (2006.01) |
| *C23C 16/26* | (2006.01) |
| *C23C 28/00* | (2006.01) |

(52) U.S. Cl.
CPC ..... *A61L 2430/24* (2013.01); *Y10T 428/12438* (2015.01); *Y10T 428/12549* (2015.01)

(56) References Cited

U.S. PATENT DOCUMENTS

| | | |
|---|---|---|
| 7,800,285 B2 | 9/2010 | Andle et al. |
| 2003/0104028 A1 | 6/2003 | Hossainy et al. |
| 2004/0220667 A1 | 11/2004 | Gelfandbein et al. |
| 2005/0100578 A1 | 5/2005 | Schmid et al. |
| 2006/0040105 A1* | 2/2006 | Sato et al. ............ 428/408 |
| 2008/0103597 A1 | 5/2008 | Lechmann et al. |
| 2010/0247885 A1* | 9/2010 | Ito et al. ............ 428/216 |
| 2011/0307068 A1 | 12/2011 | Hauert et al. |

FOREIGN PATENT DOCUMENTS

| | | |
|---|---|---|
| JP | 2008-525131 | 7/2008 |
| WO | 00/75394 | 12/2000 |
| WO | 2007/109714 | 9/2007 |
| WO | 2007123539 | 11/2007 |

OTHER PUBLICATIONS

Kiuru, M. et al. "Tantalum as a Buffer Layer in Diamond-Like Carbon Coated Artificial Hip Joints", Journal of Biomedical Materials Research Part B: Applied Biomaterials, vol. 66, 2003, pp. 425-428.

Tiainen, V-M. "Amorphous carbon as a bio-mechanical coating—mechanical properties and biological applications", Diamond and Related Materials, vol. 10, 2001, pp. 153-160.

Santavirta, S. et al. "Some relevant issues related to the use of amorphous diamond coatings for medical applications", Diamond and Related Materials, vol. 7, 1998, pp. 482-485.

Taeger, G. et al. "Comparison of Diamond-Like-Carbon and Alumina-Oxide articulating with Polyethylene in Total Hip Arthroplasty." Mat.-wiss. u. Werkstofftech. 2003, vol. 34, No. 12, pp. 1094-1100.

International Search Report and Written Opinion for International Application No. PCT/US2011/032481, dated Jul. 14, 2011.

S.L. Lee et al., "High-rate Sputter Deposited tantalum Coating on Steel for Wear and Erosion Mitigation", Jul. 6, 2001, Surface and Coatings Technology 149 (2002) 62-69, Elsevier, U.S.

International Preliminary Report on Patentability and Written Opinion issued in International Patent Application No. PCT/US2011/032481 dated Oct. 26, 2012.

Notification of Reasons for Refusal, dated Feb. 24, 2015, for Japanese Patent Application No. 2013-505136, 5 pages.

* cited by examiner

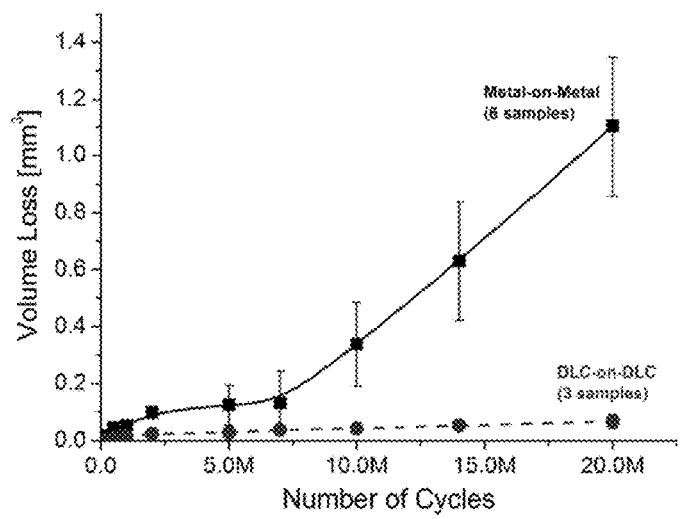
Fig. 2
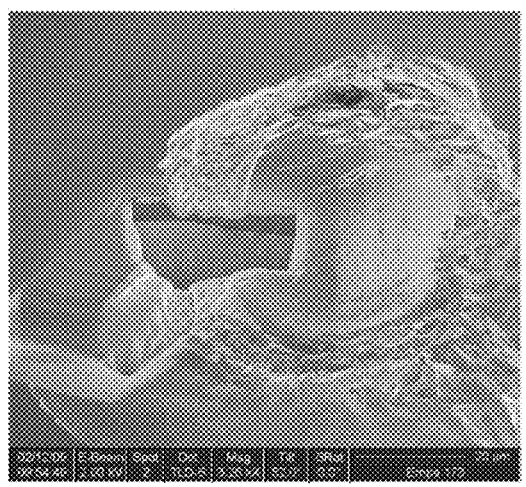 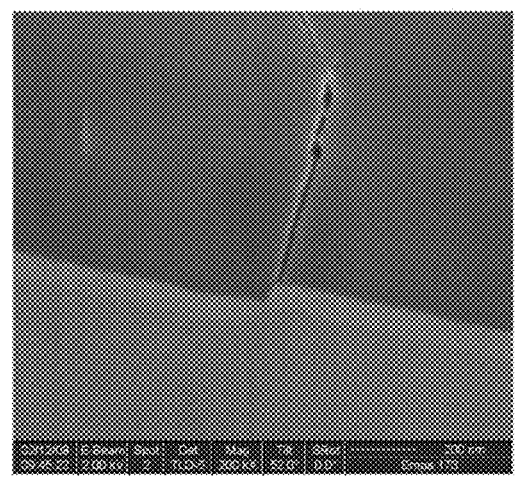
Fig. 3a                              Fig. 3b

COATING FOR A COCRMO SUBSTRATE

CROSS-REFERENCE TO RELATED APPLICATIONS

This application is a continuation in part of U.S. patent application Ser. No. 13/087,013, filed Apr. 14, 2011, which in turn claims the benefit of U.S. Provisional Patent Application No. 61/324,664, filed Apr. 15, 2010, all of which are incorporated herein by reference in their entirety.

FIELD OF THE INVENTION

The present invention generally relates to coatings on CoCrMo substrates, for example, Co28Cr6Mo substrates. More particularly the present invention relates to diamond-like carbon (DLC) coatings having excellent biostability. Some embodiments of the invention relate to a substrate with a DLC coating. Further embodiments of the invention relate to methods for applying a DLC coating to a substrate.

BACKGROUND OF THE INVENTION

The use of diamond-like carbon (DLC) coatings is known in the medical industry as a means to decrease the frictional wear of metallic components. DLC coatings have been used, for example, on articulating components of medical devices, e.g., hip replacements, to reduce surface wear. In these devices, the DLC-coated component typically articulates against a polymeric or DLC-coated counterpart. For example, a total disc replacement device for the spine may have a DLC-coated titanium alloy component that articulates against a polyethylene counterpart.

DLC coatings applied directly on to a substrate may, however, demonstrate poor adhesion stability. Due to the deposition mechanism, DLC coatings can possess excessive compressive stress in the GPa range, which favors delamination of the DLC coating from a substrate. For example, published data on certain currently available DLC-coated hip joints exhibit massive failures after 9 years in vivo.

FIG. 6 shows the revision rates of certain DLC-coated hip joint implants according to the prior art gained from a 101 implants study by Taeger et al. (Materialwissenschaften und Werkstofftechnik 2003; 34(12): 1094-1100, incorporated herein by reference in its entirety). FIG. 7 shows a hip joint head explant from the Taeger series. As can be seen, the DLC-coating has failed and caused significant wear. The origin of the failures is small delaminated spots on the DLC surface, which eventually combined to give one massive failure. Upon closer inspection, the failures appear roughly circular and can be shown to originate from a small point of failure, probably a pinhole as shown in FIG. 8. Delamination occurred in a circular fashion from an initial spot in the center.

FIG. 9 shows the delamination of the Taeger coating system originating from an artificial defect. The delamination speed rapidly increases after 240 days, at which time the storage medium was exchanged from phosphate buffered saline (PBS) to calf serum. The other data points give the energy sustained by and stored in the coating system.

Thus, there remains a need for an improved DLC coating with improved long-term adhesion in vivo.

SUMMARY OF THE INVENTION

The present invention, in some embodiments, includes a CoCrMo substrate having a coating. In some embodiments, the coated CoCrMo substrate can be used in a medical device, for example, a joint prosthesis.

In one embodiment of the present invention, a coating for a CoCrMo substrate includes four layers. In one embodiment, the four layers include a first layer including $Ta(CoCrMo)_{0.5-2.0}$, a second layer including tantalum, a third layer including tantalum carbide, and a fourth layer including diamond-like carbon (DLC). In one embodiment, the coating includes only said four layers. In one embodiment, the first layer consists essentially of $Ta(CoCrMo)_{0.5-2.0}$. In one embodiment, the second layer consists essentially of tantalum. In one embodiment, the third layer consists essentially of tantalum carbide. In one embodiment, the fourth layer consists essentially of diamond like carbon (DLC).

In some embodiments, the first layer is disposed directly on the substrate. In some embodiments, the first layer has a thickness from about 1 nm to about 5 nm, preferably from about 2 nm to about 4 nm. The first layer, according to some embodiments, has an oxygen content less than atomic %, preferably less than 3 atomic %.

In some embodiments, the second layer is disposed directly on the first layer. In some embodiments, the second layer includes alpha-tantalum. In some embodiments, the second layer is essentially free of beta-tantalum. In some embodiments, the second layer is doped with tungsten, niobium and/or titanium, for example, at about 0.1 atomic % to about 10 atomic %. In further embodiments, the second layer has a minimum thickness of 20 nm, preferably a minimum thickness of 50 nm. In yet further embodiments, the second layer has a maximum thickness of 1000 nm, preferably a maximum thickness of 200 nm. The second layer, according to some embodiments, has an oxygen content less than 5 atomic %, preferably less than 3 atomic %.

In some embodiments, the third layer is disposed directly of the second layer. In some embodiments, the third layer has a minimum thickness of 0.5 nm, preferably a minimum thickness of 4 nm. In further embodiments, the third layer has a maximum thickness of 10 nm, preferably of a maximum thickness of 6 nm. The third layer, according to some embodiments, has an oxygen content less than 5 atomic %, preferably less than 3 atomic %.

In some embodiments, the fourth layer is disposed directly on the third layer. In some embodiments, the fourth layer has a minimum thickness of 200 nm, preferably a minimum thickness of 500 nm. In some embodiments, the fourth layer has a maximum thickness of 10 μm, preferably of a maximum thickness of 5 μm. The fourth layer, according to some embodiments, has a hydrogen content of at least 1 atomic %. In further embodiments, the fourth layer has a hydrogen content of less than 35 atomic %, preferably of less than 23 atomic %.

A coating according to some embodiments of the present invention, has a mean roughness $R_a$ below 50 nm. In further embodiments, the coating has a maximum roughness $R_t$ below 200 nm. In some embodiments, the coating has a total thickness in the range of about 0.5 μm to about 10 μm.

In other embodiments, the coating is penetrated by a hole reaching the substrate. In one variation of this embodiment, the hole has a diameter $d \leq 10$.

A method for applying a coating to a CoCrMo substrate, according to some embodiments of the present invention, includes depositing an adhesion-promoting interlayer onto the substrate and depositing a DLC layer onto the adhesion-promoting interlayer. In some embodiments, a method for coating a CoCrMo substrate includes: a) inserting the CoCrMo substrate into a vacuum system; b) cleaning the CoCrMo substrate by $Ar^+$ ion bombardment; c) depositing a Ta adhesion-promoting interlayer onto the CoCrMo substrate; and d) initiating DLC growth on the Ta adhesion-promoting interlayer. In some embodiments, the Ta adhesion-promoting interlayer is deposited onto the CoCrMo substrate by sputtering, for example, at a thickness of about 10 nm to about 1 µm.

BRIEF DESCRIPTION OF THE DRAWINGS

Several embodiments of the invention will be described in the following by way of example and with reference to the accompanying drawings in which:

FIG. 2 shows the accumulated wear volume of the uncoated and coated spinal disks of FIG. 1 run in a spine simulator;

FIG. 3A shows a focused ion beam cross-cut applied at the edge of a defect found on a DLC-coated implant using the interlayer system of an embodiment of the present invention;

FIG. 3B shows a magnification of a crack stopped and contained at the interlayer system of FIG. 3A;

DETAILED DESCRIPTION

Figure 1:
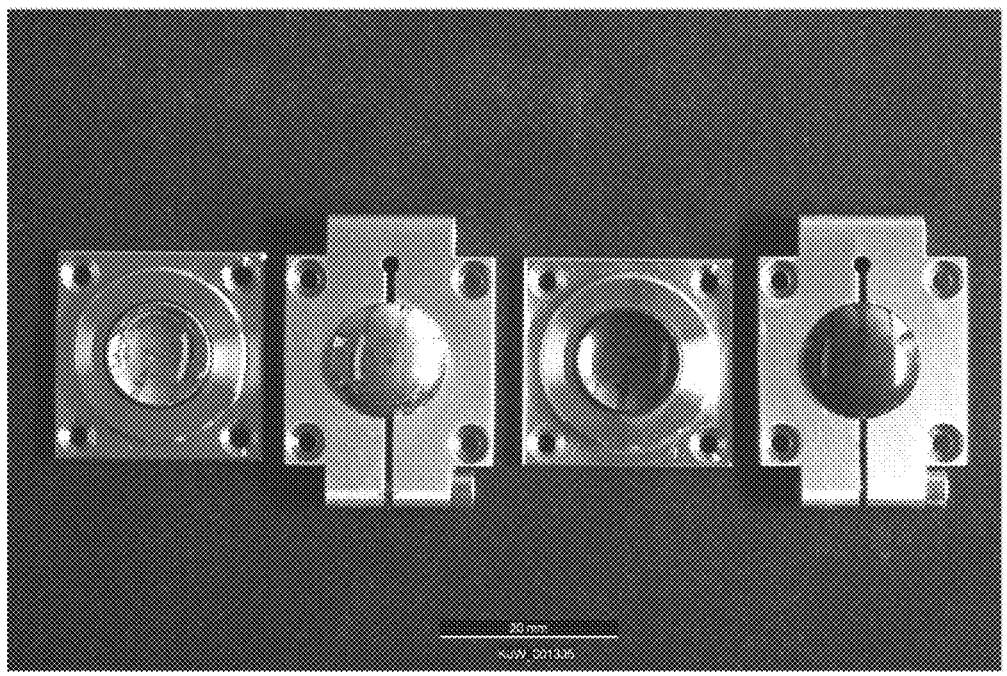
FIG. 1 shows an uncoated (left) and a coated (right) CoCrMo spinal disk implant according to one embodiment of the invention mounted on testing sockets.

The present invention, according to some embodiments, includes coatings for a substrate which may be used, for example, in medical devices. In other embodiments, the present invention includes a substrate having a coating as described herein. In some embodiments, the substrate is a component of a medical implant, for example, a joint prosthesis, a hip replacement, a spinal disc prosthesis, a bone plate, and the like. In some embodiments, the substrate is a component of a device subject to wear.

In some embodiments, the substrate is a metallic substrate. In some embodiments, the substrate includes a metal alloy. In preferred embodiments of the invention, the substrate is a cobalt-chromium-molybdenum (CoCrMo) substrate, for example, a Co28Cr6Mo substrate.

A coating in accordance with some embodiments of the present invention includes a plurality of layers. In some embodiments, each of the plurality of layers includes a different chemical composition. In some embodiments, the coating includes at least a first layer and a second layer. In some embodiments, the coating includes at least a first layer, a second layer, and a third layer. In some embodiments, the coating includes at least a first layer, a second layer, a third layer, and a fourth layer. In some embodiments, the coating includes no more than four layers. In some embodiments, the coating consists of four layers.

In some embodiments, a multi-layer coating according to present invention includes blending between adjacent layers. In some embodiments, a first layer of a coating of the present invention includes a blended interface with a second layer of the coating, in some embodiments, a second layer of a coating of the present invention includes a blended interface with a third layer of the coating. In some embodiments, a third layer of a coating of the present invention includes a blended interface with a fourth layer of the coating. In some embodiments, the blended interfaces of a multi-layer coating are each about 1 nm in thickness or less.

In some embodiments, at least one of the plurality of layers includes tantalum (Ta), a Ta alloy, or a Ta compound. In some embodiments, the coating includes three different layers wherein each of the layers includes Ta, a Ta alloy, or a Ta compound. In some embodiments, at least one of the plurality of layers, preferably the outer-most layer (i.e., the layer furthest away from the substrate), includes diamond-like carbon (DLC). In some embodiments, at least one of the plurality of layers consists essentially of DLC. In some embodiments, at least one of the Ta-containing layers serves as an adhesion-promoting interlayer to aid in chemically attaching the DLC layer to the substrate via alloying. In some embodiments, all of the Ta-containing layers serves as an adhesion-promoting interlayer.

In some embodiments, a coating in accordance with the present invention includes a first layer disposed directly on a substrate, e.g., a CoCrMo substrate. In some embodiments, the first layer is composed of a material different than the substrate. In some embodiments, the first layer includes a CoCrMo alloy. In some embodiments, the first layer consists essentially of a CoCrMo alloy. In some embodiments, the first layer includes tantalum (Ta). In some embodiments, the first layer consists essentially of tantalum. In some embodiments, the first layer includes a tantalum alloy. In some embodiments, the first layer consists essentially of a tantalum alloy. In some embodiments, the first layer includes Ta(CoCrMo), e.g., Ta(CoCrMo)$_{0.5-2.0}$. In some embodiments, the first layer consists essentially of Ta(CoCrMo), e.g., Ta(CoCrMo)$_{0.5-2.0}$. In some embodiments, the first layer has an oxygen content less than 5 atomic %, preferably less than 3 atomic %. In some embodiments, the first layer has an oxygen content less than 2 atomic %. In some embodiments, the first layer has an oxygen content less than 1 atomic %. In some embodiments, the first layer has an oxygen content less than 0.5 atomic %. In some embodiments, high oxygen content (e.g., greater than 5 atomic %) may weaken the interface of the first layer and enable various failure mechanisms (e.g., cracking). When present at high levels (e.g., greater than 5 atomic %), oxygen in some embodiments may terminate potential interatomic bonds and induce phase changes that may make the coating brittle and susceptible to corrosive attack.

In some embodiments, the first layer has a thickness of at least 1 nm. In some embodiments, the first layer has a thickness of at least 2 nm. In some embodiments, the first layer has a thickness of at least 3 nm. In some embodiments, the first layer has a thickness of at least 4 nm. In some embodiments, the first layer has a thickness of at least 5 nm. In some embodiments, the first layer has a thickness of about 1 nm to about 5 nm, preferably about 2 nm to about 4 nm. In some embodiments, the first layer has a thickness of 1 nm to 5 nm, preferably 2 nm to 4 nm. In some embodiments, the first layer has a thickness of no more than 5 nm. In some embodiments, the first layer has a thickness of no more than 4 nm.

In some embodiments, a coating according to the present invention further includes a second layer disposed directly on the first layer, such that the first layer is positioned between the substrate and the second layer with no intervening layer. In some embodiments, there is blending between the first layer and the second layer at their interface. In some embodiments, the blended interface is no more than 1 nm in thickness, in some embodiments, the second layer is composed of a material different than the substrate and the first layer.

In some embodiments, the second layer includes tantalum. In some embodiments, the second layer consists essentially of tantalum. In some embodiments, the second layer includes alpha-tantalum. In some embodiments, the second layer consists essentially of alpha-tantalum. Alpha-tantalum has been found to be, according to some embodiments, a macroseopically ductile phase whereas other tantalum phases (e.g., beta-tantalum) may be relatively brittle. By excluding relatively brittle beta-tantalum from the coating, a more ductile coating may be obtained in some embodiments. In some embodiments, a more ductile coating provides better long-term adhesion of the coating to the substrate. Therefore, in preferred embodiments, the second layer is substantially free of beta-tantalum. In some embodiments, the second layer includes amorphous alpha tantalum and nanocrystalline alpha tantalum. In some embodiments, the second layer consists essentially of amorphous alpha tantalum and nanocrystalline alpha tantalum. Moreover, in some embodiments, the second layer has an oxygen content less than 5 atomic %, preferably less than 3 atomic %. Higher oxygen content (e.g., greater than 5 atomic %), in some embodiments, may lead to beta phase tantalum formation, which can be macroscopically brittle. Accordingly in preferred embodiments it is desirable to keep the oxygen level, during deposition sufficiently low so that the resulting coating layer has, for example, an oxygen content less than 5 atomic %, preferably less than 3 atomic %. In some embodiments, the second layer has an oxygen content less than 2 atomic %. In some embodiments, the second layer has an oxygen content less than 1 atomic %. In some embodiments, the second layer has an oxygen content less than 0.5 atomic %. When present at high levels (e.g., greater than 5 atomic %), oxygen in some embodiments may terminate potential interatomic bonds and induce phase changes that may make the coating brittle and susceptible to corrosive attack.

In further embodiments, the tantalum is deposited with alpha-phase-stabilizing dopands. In some embodiments, the second layer includes Ta (e.g., alpha-tantalum) doped with niobium (Nb) tungsten (W), and/or titanium (Ti). In some embodiments, the second layer consists essentially of Ta (e.g., alpha-tantalum) doped with niobium (Nb), tungsten (W), and/or titanium (Ti). Nb, W, and/or Ti in some of these embodiments may be present in the second layer at about 0.1 atomic % to about 10 atomic %. Doping with alpha-phase-stabilizing dopands such as Nb, W, and/or Ti, according to some embodiments, leads to a stabilization of the alpha-phase composition and an increase of the oxygen tolerance, i.e., the level of oxygen contamination that would still allow for long-term adhesion of the coating to the substrate. In some embodiments, a layer including tantalum doped with alpha-phase-stabilizing dopands may have an oxygen tolerance that allows for an oxygen content greater than 3 atomic %. In some embodiments, a layer including tantalum doped with alpha-phase-stabilizing dopands may have an oxygen tolerance that allows for an oxygen content greater than 5 atomic %.

In some embodiments, the second layer has a thickness of at least 20 nm. In some embodiments, the second layer has a thickness of at least 30 nm. In some embodiments, the second layer has a thickness of at least 40 nm. In some embodiments, the second layer has a thickness of at least 50 nm. In some embodiments, the second layer has a thickness of at least 100 nm. In some embodiments, the second layer has a thickness of about 20 nm to about 1000 nm, preferably about 50 nm to about 200 nm. In some embodiments, the second layer has a thickness of 20 nm to 1000 nm, preferably 50 nm to 200 nm. In some embodiments, the second layer has a thickness of no more than 1000 nm. In some embodiments, the second layer has a thickness of no more than 500 nm. In some embodiments, the second layer has a thickness of no more than 200 nm.

In some embodiments, a coating according to the present invention further includes a third layer disposed directly on the second layer, such that the first layer is positioned between the substrate and the second layer, and the second layer is positioned between the first layer and the third layer. In some embodiments, the third layer is composed of a material different than the substrate, the first layer, and the second layer. In some embodiments, there is no intervening layer between the second layer and the third layer. In some embodiments, there is blending between the second layer and the third layer at their interface.

In some embodiments, a third layer includes tantalum. In some embodiments, a third layer consists essentially of tantalum. In some embodiments, the third layer includes a tantalum compound. In some embodiments, the third layer consists essentially of a tantalum compound. In some embodiments, the third layer includes or consists essentially of a carbide. In some embodiments, the third layer consists essentially of a carbide. In some embodiments, the third layer includes tantalum carbide. In some embodiments, the third layer consists essentially of tantalum carbide. In some embodiments, the third layer has ma oxygen, content less than 5 atomic %, preferably less than 3 atomic %. In some embodiments, the third layer has an oxygen content less than 2 atomic %. In some embodiments, the third layer has an oxygen content less than atomic %. In some embodiments, the third layer has an oxygen content less than 0.5 atomic %. When present at high levels (e.g., greater than 5 atomic %), oxygen in some embodiments may terminate potential interatomic bonds and induce phase changes that may make the coating brittle and susceptible to corrosive attack.

In some embodiments, the third layer has a thickness of at least 0.5 nm. In some embodiments, the third layer has a thickness of at least 1 nm. In some embodiments, the third layer has a thickness of at least 2 nm. In some embodiments, the third layer has a thickness of at least 3 nm. In some embodiments, the third layer has a thickness of at least 4 nm. In some embodiments, the third layer has a thickness of about 0.5 nm to about 10 nm, preferably about 4 nm to about 6 nm. In some embodiments, the third layer has a thickness of 0.5 nm to 10 nm, preferably 4 nm to 6 nm. In some embodiments, the third layer has a thickness of no more than 10 nm. In some embodiments, the second layer has a thickness of no more than 6 nm.

In some embodiments, a coating according to the present invention further includes a fourth layer disposed directly on the third layer, such that the first layer is positioned between the substrate and the second layer, the second layer is positioned between the first layer and the third, and the third layer is positioned between the second layer and the fourth layer. In some embodiments, the fourth layer is composed of a material different than the substrate, the first layer, the second layer, and the third layer. In some embodiments, there is no intervening layer between the third layer and the fourth layer. In some embodiments, there is blending between the third layer and the fourth layer at their interface.

In some embodiments, the fourth layer includes diamond-like carbon (DLC). In some embodiments, the fourth layer consists essentially of diamond-like carbon (DLC). In some embodiments, the fourth layer has a hardness of about 10 GPa to about 80 GPa as measured by nanoindentation. In some embodiments, the fourth, layer has a hardness greater than 10 GPa as measured by nanoindentation. In some embodiments, the fourth layer has a hardness greater than 20 GPa as measured by nanoindentation. In some embodiments, the fourth layer has a hardness greater than 30 GPa as measured by nanoindentation. In some embodiments, the fourth layer has a hardness greater than 40 GPa as measured by nanoindentation. In some embodiments, the fourth layer has a hardness greater than 50 GPa as measured by nanoindentation. In some embodiments, the fourth layer has a hardness greater than 60 GPa as measured by nanoindentation, in some embodiments, the fourth layer has a hardness greater than 70 GPa as measured by nanoindentation. In some embodiments, the fourth layer has a hardness greater than 80 GPa as measured by nanoindentation.

In some embodiments, a high hydrogen content (e.g., greater than 35 atomic %) may result in reduced hardness of the fourth layer due to increased hydrogen bonding. Accordingly, in preferred embodiments, the fourth layer has a hydrogen content of no more than 35 atomic %. In some embodiments, the fourth layer has a hydrogen content of less than 35 atomic %, preferably less than 23 atomic %. In some embodiments, the fourth layer has a hydrogen content of less than 15 atomic %. In some embodiments, the fourth layer has a hydrogen content of at least 1 atomic %.

In some embodiments, the fourth layer has a thickness of at least 200 nm. In some embodiments, the fourth layer has a thickness of at least 300 nm. In some embodiments, the fourth layer has a thickness of at least 400 nm. In some embodiments, the fourth layer has a thickness of at least 500 nm. In some embodiments, the fourth layer has a thickness of at least 1 µm. In some embodiments, the fourth layer has a thickness of about 200 nm to about 10 µm, preferably about 500 nm to about 5 µm. In some embodiments, the fourth layer has a thickness of 200 nm to 10 µm, preferably 500 nm to 5 µm. In some embodiments, the fourth layer has a thickness of no more than µm. In some embodiments, the second layer has a thickness of no more than 5 µm.

A coating according to an embodiment of the present invention having a first layer, second layer, third layer, and fourth layer as described herein preferably has a total thickness of about 500 nm to about 10 µm, and more preferably of about 2 µm to about 5 µm. In variations of this embodiment, the coating has a total thickness of no more than 10 µm, preferably no more than 5 µm.

In further embodiments, a coating according to the present invention has a mean roughness $R_a$ of less than 50 nm, preferably less than 25 nm. In some embodiments, the maximum roughness $R_t$ of the coating is less than 200 nm, preferably less than 150 nm. The values for roughness (e.g., $R_a$ and $R_t$) as mentioned herein are obtained by measurement as an average of four 100 µm traces taken at the sample surface with a diamond stylus profilometer. In some embodiments, the coating of the present invention is preferably deposited on a clean, polished substrate surface having a mean roughness less than 50 nm and a maximum roughness less than 200 nm.

In some particular embodiments, a coating of the present invention may include one or more holes. In one such embodiment, one or more holes pass through the entire thickness of the coating. In some embodiments, the one or more holes extend only partially through the entire thickness of the coating. In some embodiments, one or more holes are formed by substrate inhomogeneity. In some embodiments, one or more holes are formed by the presence of an impurity (e.g., dust) during the formation of the coating. In some embodiments, a coating includes one or more holes, each hole having a maximum width of about 10 µm. In other embodiments, each hole has a maximum width of about 4 µm. In some embodiments, a coating includes one or more substantially circular holes having a diameter d of no more than 10 µm, preferably no more than 4 µm. In some embodiments, a coating of the present invention has no holes.

Coatings according to embodiments of the invention may provide high resistance towards corrosion-assisted delamination mechanisms such that a coating integrity of at least 20 years, preferably at least 30 years, in vivo can be expected from the coatings. Crack growth speed along the interfaces of a coating according to some embodiments is lower than 0.011 µm per day in simulated body fluid (phophate buffered saline, calf serum) and in vivo. The measured DLC-on-DLC wear with a coating in some embodiments is as low as 0.005 mm$^3$/Mio Cycles.

One embodiment of the present invention also includes methods for producing a coating on a substrate, e.g., a CoCrMo substrate. Exemplary methods of the present invention may be used to produce the coatings described herein. In one embodiment, a method for producing a DLC coating on a substrate includes depositing an adhesion-promoting interlayer onto the substrate and depositing a DLC layer onto the adhesion-promoting interlayer.

In some embodiments, depositing an adhesion-promoting interlayer includes depositing Ta onto the substrate, for example, via sputtering. In some embodiments, a layer of about 10 nm to about 1 µm of Ta is deposited onto the substrate. In some embodiments, depositing Ta onto a CoCrMo substrate results in a first layer including a Ta(CoCrMo) alloy, e.g., Ta(CoCrMo)$_{0.5-2.0}$, the substrate surface. In some embodiments, depositing Ta onto the CoCrMo substrate further results in a second layer including Ta, e.g., alpha-tantalum. In some embodiments, subsequent depositing of a DLC layer onto the adhesion-promoting interlayer results in the formation of a third layer including Ta carbide and a fourth layer including DLC. In some embodiments, the DLC layer is deposited using a vapor deposition process, for example, plasma assisted chemical vapor deposition (PACVD). In some embodiments, depositing Ta and depositing DLC are preferably performed under vacuum (e.g., at a pressure of about $5 \cdot 10^{-5}$ Pa or less).

In some embodiments, the substrate may be cleaned prior to the deposition of the adhesion-promoting interlayer, for example, to remove any dirt or foreign substances that may interfere with the deposition steps. In some embodiments, cleaning the substrate optionally includes precleaning the substrate using one or more chemical solvents (e.g., acetone and/or ethanol). In further embodiments, the substrate is cleaned via ion bombardment (e.g., $Ar^+$ bombardment) to remove a thin (e.g., <1 µm) layer of material from the substrate surface. In preferred embodiments, cleaning the substrate includes removal of oxidic surface layers from the substrate (e.g., by sputter cleaning). In some embodiments, removal of oxidic surface layers from the substrate produces a reactive surface on the substrate.

In some exemplary embodiments, once the substrate (e.g. a CoCrMo substrate) is treed of oxidic surface layers, the sputtering of tantalum provides neutral tantalum atoms on the substrate surface. These neutral tantalum atoms form intermetallic phases with the substrate surface producing a first layer featuring interdiffusion and atomic mixing of the tantalum and the substrate material. With a CoCrMo substrate according to certain embodiments, this results in the alloying of the tantalum and the CoCrMo substrate material, producing a first layer of Ta(CoCrMo), e.g., Ta(CoCrMo)$_{0.5-2.0}$. As additional tantalum is sputtered, a second layer establishes on the first layer once the mixing and interdiffusion range of the tantalum into the substrate surface is exceeded. In some embodiments, the interdiffusion range is equal to the thickness of the first layer. The second layer includes primarily tantalum and, in some embodiments, possible minor contaminations in the vacuum chamber such as oxygen. A third layer is formed according to further embodiments when the deposition of tantalum is switched to plasma assisted chemical vapor deposition (PACVD) of acetylene, which leads to impingement of $C_xH_y$ species onto the surface of the second layer and penetration according to the ballistic energy of the $C_xH_y$ species. The implanted $C_xH_y$ species form a carbide layer with the tantalum surface of the second layer (e.g., a Ta carbide layer). Once the ballistic range of the $C_xH_y$ species (e.g., the thickness of the third layer and interdiffusion) is exceeded, a fourth layer of DLC grows via a "subplantation" process as, for example, described in Lifshitz et al., "Subplantation model for film growth from hyperthermal species," *Physical Review B*, Vol. 41, No. 15, 15 May 1990, which is incorporated herein by reference in its entirety.

An example method for coating a substrate according to one embodiment of the present invention includes one or more of the following:

1. Precleaning of the substrate for about five minutes, for example, by immersion into a 1:1 mixture of acetone and ethanol in an ultrasonic cleaner.
2. Inserting the substrate into a vacuum system chamber featuring an RF-powered sample holder and a magnetron sputtering apparatus and establishing a base pressure, for example, of less than $5 \cdot 10^{-5}$ Pa.
3. Cleaning of the substrate by argon ion ($Ar^+$) bombardment, for example, by igniting an Ar plasma by application of a 13.56 MHz radiofrequency voltage to the sample holder with respect to the grounded chamber walls. Through automatic adjustment of hie RF power, an RF bias of about −600 V between these points may be established at an Ar pressure of about 2 Pa. In some embodiments, this cleaning step results in removal of approx. 140 nm of material from the substrate surface by sputtering and may take about 30 min.
4. Cleaning of the Ta sputtering target by burn-in, for example, the Ta target is sputtered at high power behind an appropriate cover (shutter) while the substrate is further kept from oxidizing by argon bombardment. In some embodiments, the working pressure is about $2 \cdot 10^{-1}$ Pa Argon and the duration of this step is from about 2 to about 5 min. The DC magnetron operating parameters according to some embodiments are U=−435 V, (P=200 W, I=450 mA). The RE-bias used in some embodiments for substrate ion bombardment is about −300 V.
5. Depositing a Ta adhesion promoting interlayer (e.g., of thickness 100 nm) onto the substrate. To facilitate this, in some embodiments the shutter is opened while simultaneously ceasing the ion bombardment onto the substrate surface. The DC sputtering parameters may be the same as the previous step, and the RF bias on substrate holder is 0 V. An example deposition rate of Ta is about 20 nm/min according to some embodiments, which therefore results in a Ta thickness of about 100 nm after about five minutes.
6. Deactivating of the DC magnetron while simultaneously initiating DLC growth. In some embodiments, growth of DLC can be performed by a PV) or CVD process, preferably plasma assisted chemical vapor deposition (PACVD) using acetylene gas and a bias voltage applied to the substrate holder. Example working pressures may be about 2.5 Pa $C_2H_2$ with an RF bias on the substrate holder of about −600 V. In some embodiments the deposition rate of DLC is about 30 nm/min. The resulting DLC layer thickness, in some embodiments, is about 2 μm to about 4 μm after a duration of about 60 to about 120 min.
7. Allowing the coated substrate to cool in vacuum and removing the coated substrate from the chamber.

In some embodiments, the oxygen (contaminant) flow into the process chamber can be determined from mass spectrometry measurements provided that the Ar flow into the chamber is known. In the example method above, the oxygen flow is purposefully adjusted before process start via the m/e ($O_2^+$ (32)/$Ar^+$(40)) ratio at a known Ar flow using an oxygen leak valve. The resulting chemical composition of the adhesion promoting interlayer (second layer) can be obtained from characterization methods like x-ray photoelectron spectroscopy (XPS) and is also characteristic for the oxygen content in layers (third layer) and (first layer). This chemical information can in turn be linked to layer performance in appropriate tests (spine simulators, delamination tests). This permits defining tolerance limits for oxygen and to implement an on-line monitoring system for interlayer stability for a given deposition system and a given process setting.

The substrate on which the coatings of the present invention may be deposited can be flat or curved. For example, the substrate may be particularly shaped for ball-on-socket articulation or for point contact articulations. Due to its elevated hardness (e.g., about 10 GPa to about 80 GPa as measured by nanoindentation), the multilayer coating according to some embodiments of the present invention may withstand high mechanical stress encountered with point contact conditions (e.g., 4 GPa compressive stress). The DLC-coated part can be favorably used in combination with a counterpart substrate bearing the same coating according to embodiments of the invention.

FIG. 1 shows an example uncoated (left) and a coated (right) CoCrMo spinal disk implant provided with a coating according to an embodiment of the invention resistant to corrosion-assisted delamination. The coating system for this sample included a 3 nm, thick Ta(CoCrMo) layer, a 100 nm thick Ta layer, a 5 nm thick Ta-carbide layer and a 4 μm thick DLC layer. The oxygen contamination in the layer system was verified to be below 3 atomic % inside the adhesion promoting layer system (as measured in the Ta layer) by monitoring of the chamber gas composition during deposition and related device calibrations. The samples shown in FIG. 1 withstood more than 70 million load cycles in a spine simulator setup. Tests in a spinal wear simulator setup show that the wear of such coated implants is significantly reduced compared to uncoated metal-on-metal tribopairs (FIG. 2).

The accumulated wear volume shown in FIG. 2 was calculated from gravimetric measurements after a cleaning process as specified in ISO 14242-2 (densities DLC 2.8 g/cm$^3$; CoCrMo: 8.29 g/cm$^3$). The metal wear observed was caused by roughening of the initially smooth metal surface. Furthermore, nanoscale analysis showed that plastic impressions of the hard coating ("eggshell effect") do not cause cracks to propagate along the coating-substrate interface, which could lead to delamination and implant failure.

FIGS. 3A and 3B show an example defect caused by a hard particle inside the tribocontact ("eggshell effect"). The coating shown in FIGS. 3A and 3B has an oxygen content of less than 0.3 atomic %. As shown in FIG. 3B, this system has been found to be tolerant towards isolated defects; small defects caused, for example by scratches penetrating into the substrate, will not expand via one of the described failure mechanisms and coalesce into macroscopic defects, leading to implant failure, such as observed on prior art implants. Moreover, long-time monitoring of Rockwell indents, holes punctured into the surface by means of a Rockwell tip having a conical diamond tip with an angle of about 120 degrees at a defined load (example here: 1500 N), while immersing the implants in saline solution results in no observed tendency of stress-corrosion cracking.

Figure 4:
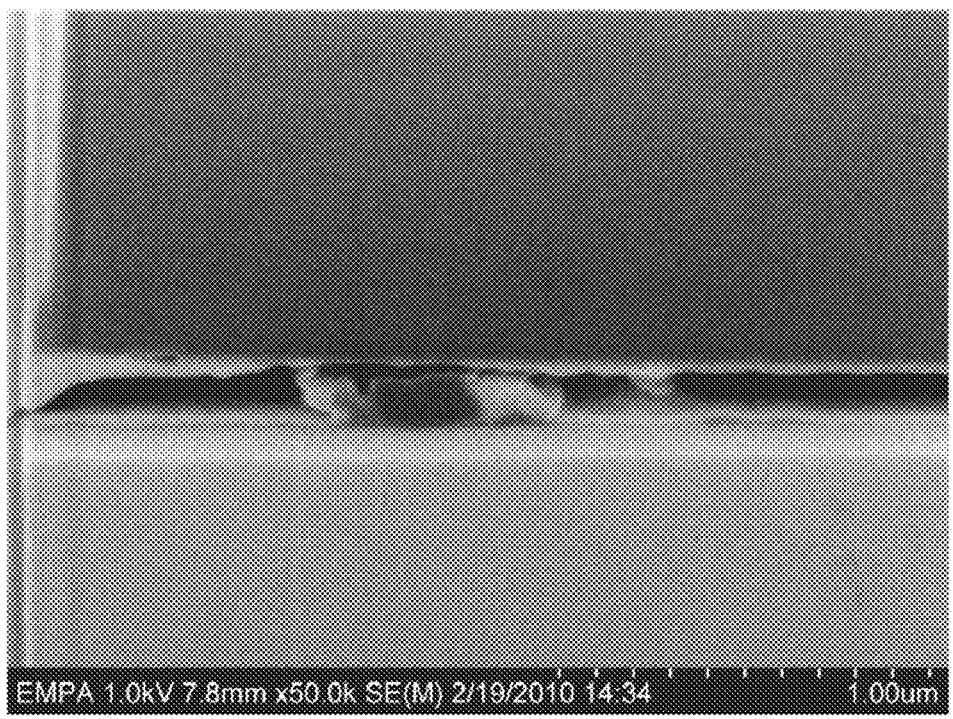
FIG. 4 shows a tantalum-based interlayer system according to another embodiment with an oxygen content of 3.5 atomic %.

Layers with an oxygen content exceeding the limits defined according to embodiments of the invention may propagate the crack along the third layer. For example, as shown in FIG. 4, a layer system in one embodiment having an oxygen content of 3.5 atomic % may propagate a crack along the third layer, leading to possible delamination and implant failure after several thousand loading cycles.

Figure 5:
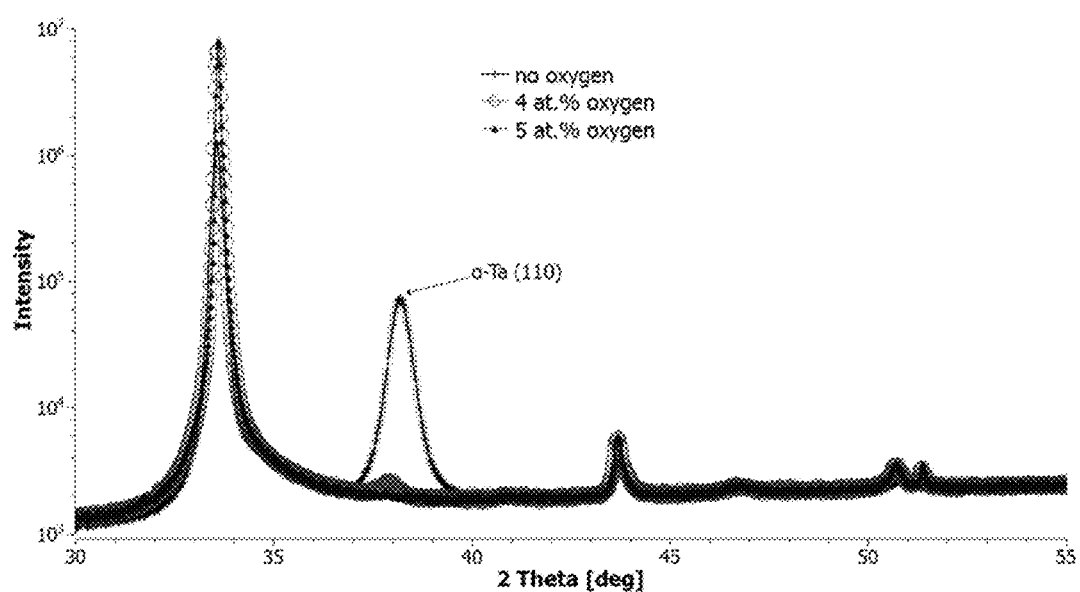
FIG. 5 shows XRD scans of Ta layers featuring different oxygen contaminations as grown in accordance with embodiments of the present invention.
Figure 6:
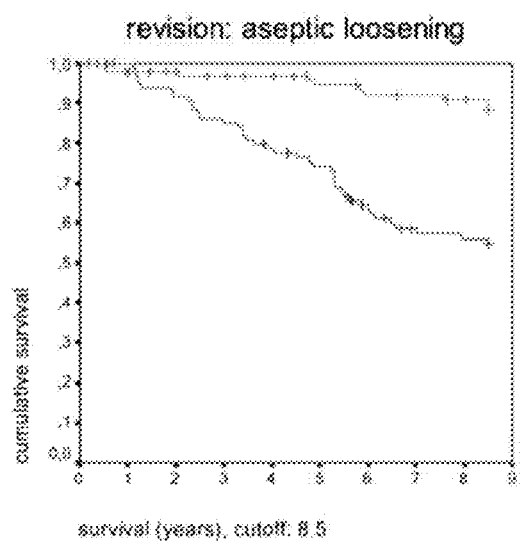
FIG. 6 shows the revision rates of DLC-coated hip joint implants according to the prior art.
Figure 7:
FIG. 7 shows a hip joint head explant according to the prior art with a failed DLC-coating causing significant wear.
Figure 8:
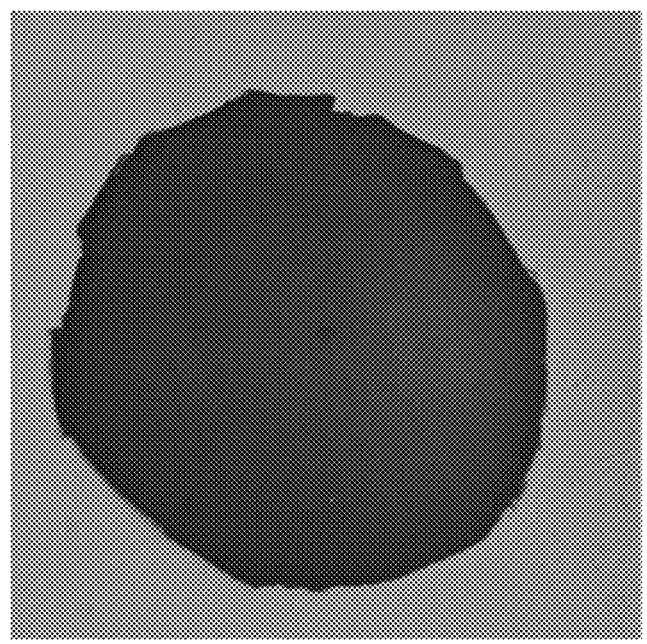
FIG. 8 shows the delamination on an implant DLC layer according to the prior art (SEM image)
Figure 9:
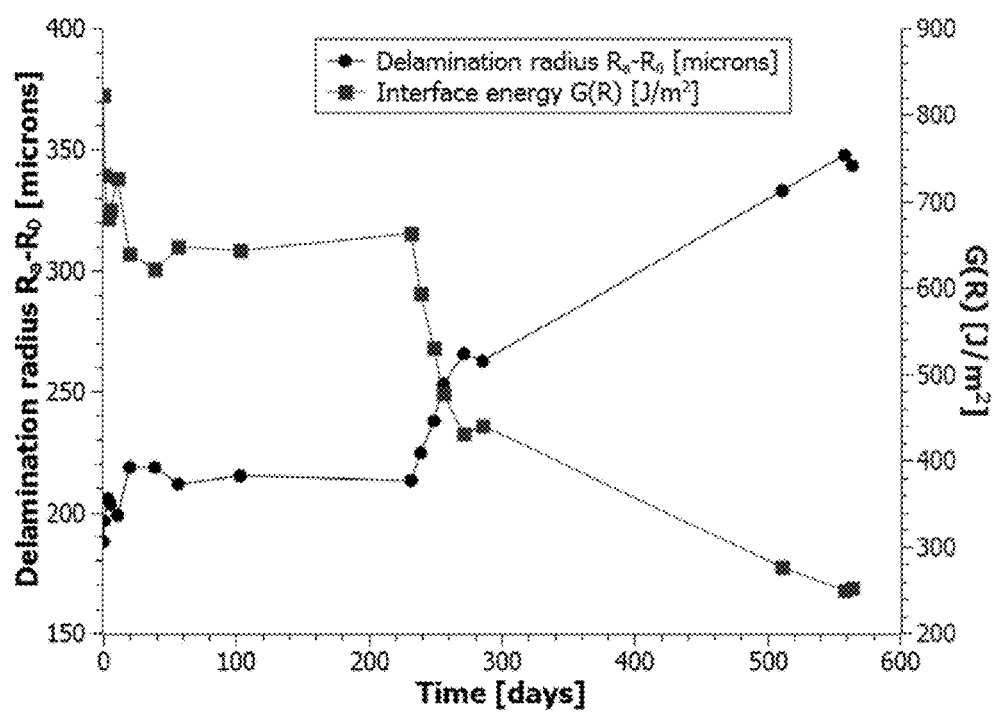
FIG. 9 shows the delamination of a coating system according to the prior art originating from an artificial defect.

As shown in FIG. 5 X-ray diffraction measurements (XRD) on oxygen contaminated. Ta interlayers (Bragg-Brentano geometry) reveal that the alpha-phase tantalum ("α-Ta (110)") peak disappears at rising oxygen contamination levels. The alpha-phase peak is caused by constructive interference of the x-rays on planes of crystallites featuring the respective lattice spacing, as shown here, the spacing of alpha-tantalum in 110 lattice direction. FIG. 5 shows the alpha-phase peak disappears with the addition of oxygen, indicating a structural change of the adhesion promoting interlayer; the alpha phase disappearance is linked to a deterioration of the interlayer properties caused by increasing oxygen contamination.

The tantalum interlayer structure is thus assumed to change completely. The phase change occurs simultaneous to mechanical failure of the test samples. It is thus assumed that the phase change leads to loss of stability of the Ta/DLC interface as observed with Focused Ion Beam (FIB), a method using a jet of accelerated ions to cut through a sample, delivering a highly polished cross-cut particularly suited for analysis with a high resolution SEM. This may open another route to diagnose the stability of the Ta interlayer.

Referring to FIG. 5, the intensities and widths of the main peaks indicate that the tantalum layer contains beta-phase tantalum, nano-crystalline alpha-phase tantalum and amorphous tantalum. The 2 theta (or 2-θ) peak of alpha-phase tantalum is found at 38° and the 2-θ peak of beta-phase tantalum is found at 34° as one of skill in the art will understand. The following peak intensities and full-width-half-maximum values can be established from FIG. 5 for the three samples (no oxygen, 4 at. % oxygen, 5 at. % oxygen)

TABLE 1

Peak Intensities And Full-Width-Half-Maximum Values Established Based On FIG. 5

| Sample | Beta-phase tantalum (002) Intensity [a.u.] | Beta-phase tantalum (002) FWHM (deg) | Alpha-phase tantalum (110) Intensity [a.u.] | Alpha-phase tantalum (110) FWHM [deg] |
|---|---|---|---|---|
| No oxygen | 265151 | 0.20 | 34855 | 0.45 |
| 4 at. % oxygen | 709636 | 0.10 | 1738 | 1.43 |
| 5 at. % oxygen | 729471 | 0.08 | — | — |

The peak intensities can be compared using the respective structure factors $F_x$ and the plane multiplicity $m_x$. The relationship, $F_x^2 \cdot mx$ links the observed intensity to the actual crystal volume involved in scattering. For alpha-phase tantalum (110), F=14, m=12 giving an intensity factor of 2352. For beta-phase tantalum (002), F=2, m=2 giving an intensity factor of 8. Therefore, at comparable layer thickness, the total crystalline volume in the samples can be calculated from the well known equation of Volume=Intensity (beta,(002))/8+ intensity (alpha,(110))/2352.

TABLE 2

Comparison of The peak intensities of Table 1 Using The Respective Structure Factors $F_x$ And The Plane Multiplicity $m_x$

| Sample | Total crystalline volume [a.u.] | Beta-phase tantalum (002) (estimated, wt. %) | Alpha-phase tantalum (110) (estimated, wt. %) | Amorphous tantalum (estimated, wt. %) |
|---|---|---|---|---|
| No oxygen | 33159 | 36.3 | 0.016 | 63.7 |
| 4 at. % oxygen | 88705 | 97.3 | $8.1 \cdot 10^{-4}$ | 2.7 |
| 5 at. % oxygen | 91184 | 100 | 0 | 0 |

Because the layer volume was comparable at all oxygen levels, a non-crystalline. i.e. amorphous, component is the source of the undetected amount of the crystalline volume. Therefore, the oxygen-free sample contains a high amount of amorphous tantalum. This is further corroborated by calculating the crystallite size from the peak FWHM using the well-known Scherrer Formula.

TABLE 3

Caculated Crystallite Size From The Peak FWHM (Using Scherrer Formula)

| Sample | Beta-phase tantalum (002) crystallite size [nm] | Alpha-phase tantalum (110) crystallite size [nm] |
|---|---|---|
| No oxygen | 43.3 | 19.5 |
| 4 at. % oxygen | 86.7 | 6.1 |
| 5 at. % oxygen | 108.3 | — |

This data demonstrates that the oxygen-free layer contains smaller crystallites, evidence of a, nanocrystalline and amorphous structure for the tantalum layer. As amorphous materials possess high elastic properties, amorphous tantalum is beneficial as adhesive interlayer as claimed in this disclosure.

The coatings according to the above examples can be adapted to hip joints and other medical devices and implants without loss of functionality. Other example medical devices for which a coating according to embodiments of the present invention may be used include Kirschner wires, intramedullary nails, bone screws, dental implants. In some embodiments, a coating according to the present invention may be useful for other devices subject to wear, including non-medical devices, such as for example, machine parts, gears, and tools. In some embodiments, a coating according to the present invention may be particularly useful for devices subject to wear at temperatures below 300° C.

It should be understood that various changes, substitutions, and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure herein, processes, machines, manufacture, composition of matter, means, methods, or steps, presently existing or later to be developed that perform substantially the same function or achieve substantially the same result as the corresponding embodiments described herein may be utilized according to the present invention.

The invention claimed is:

1. A coating for a CoCrMo substrate comprising:
   a first layer comprising $Ta(CoCrMo)_{0.5-2.0}$;
   a second layer comprising amorphous alpha-tantalum and nanocrystalline alpha-tantalum;
   a third layer comprising tantalum carbide; and
   a fourth layer comprising diamond-like carbon (DLC),
   wherein the coating contains no beta-tantalum.

2. The coating according to claim 1, wherein the first layer has a thickness of about 1 nm to about 5 nm.

3. The coating according to claim 1, wherein the second layer has a thickness of at least 20 nm.

4. The coating according to claim 1, wherein the third layer has a thickness of at least 0.5 nm.

5. The coating according to claim 1, wherein the fourth layer has a thickness of at least 200 nm.

6. The coating according to claim 1, wherein the fourth layer has a hydrogen content of less than 35 atomic %.

7. The coating according to claim 1, wherein the first layer, the second layer, and the third layer each has an oxygen content lower than 5 atomic %.

8. The coating according to claim 1, wherein the coating has a mean roughness $R_a$ below 50 nm.

9. The coating according to claim 1, wherein the coating has a maximum roughness $R_t$ below 200 nm.

10. The coating according to claim 1, wherein total thickness of all four layers is in the range of about 0.5 μm to about 10 μm.

11. The coating according to claim 1, wherein the second layer is doped with tungsten, niobium or titanium.

12. A device comprising a substrate with a coating according to claim 1.

13. The device according to claim 12, wherein said coating is penetrated by a hole reaching the substrate.

14. The device according to claim 13, wherein said hole has a diameter d≤10 micrometers.

15. The device according to claim 12, wherein the device is a joint prosthesis.

16. The coating according to claim 1, wherein the second layer consists essentially of amorphous alpha tantalum and nanocrystalline alpha tantalum.

17. A coating for a CoCrMo substrate comprising:
   a first layer comprising $Ta(CoCrMo)_{0.5-2.0}$;
   a second layer comprising amorphous alpha-tantalum and nanocrystalline alpha-tantalum;
   a third layer comprising tantalum carbide; and
   a fourth layer comprising diamond-like carbon (DLC).

18. The coating according to claim 17, wherein the second layer consists essentially of amorphous alpha tantalum and nanocrystalline alpha tantalum.

19. The coating according to claim 17, wherein the second layer is essentially free of beta tantalum.

20. The coating according to claim 17, wherein the first layer has a thickness of 1 nm to 5 nm, the second layer has a thickness of 20 nm to 1000 nm, and the third layer has a thickness of about 0.5 nm to 10 nm.

* * * * *